United States Patent
Nesta et al.

(10) Patent No.: US 9,801,795 B2
(45) Date of Patent: *Oct. 31, 2017

(54) ORAL CARE COMPOSITIONS AND METHODS

(71) Applicant: COLGATE-PALMOLIVE COMPANY, New York, NY (US)

(72) Inventors: Jason Nesta, Cedar Knolls, NJ (US); Gregory Szewczyk, Flemington, NJ (US); Evangelia Arvanitidou, Princeton, NJ (US); Alexander Mijalis, Shreveport, LA (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/106,652

(22) PCT Filed: Dec. 20, 2013

(86) PCT No.: PCT/US2013/076887
§ 371 (c)(1),
(2) Date: Jun. 20, 2016

(87) PCT Pub. No.: WO2015/094333
PCT Pub. Date: Jun. 25, 2015

(65) Prior Publication Data
US 2016/0331651 A1    Nov. 17, 2016

(51) Int. Cl.
| | | |
|---|---|---|
| *A61K 8/81* | (2006.01) | |
| *A61K 8/22* | (2006.01) | |
| *A61K 8/24* | (2006.01) | |
| *A61Q 11/00* | (2006.01) | |
| *C08L 43/02* | (2006.01) | |
| *A61K 8/34* | (2006.01) | |
| *A61K 8/37* | (2006.01) | |
| *A61K 8/60* | (2006.01) | |
| *A61K 8/86* | (2006.01) | |

(52) U.S. Cl.
CPC .......... *A61K 8/22* (2013.01); *A61K 8/24* (2013.01); *A61K 8/345* (2013.01); *A61K 8/347* (2013.01); *A61K 8/37* (2013.01); *A61K 8/60* (2013.01); *A61K 8/8147* (2013.01); *A61K 8/8164* (2013.01); *A61K 8/86* (2013.01); *A61Q 11/00* (2013.01); *C08L 43/02* (2013.01); *A61K 2800/5422* (2013.01); *A61K 2800/5424* (2013.01); *A61K 2800/592* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 4,892,724 A | 1/1990 | Amjad | |
| 5,425,953 A | 6/1995 | Sintov | |
| 5,599,527 A * | 2/1997 | Hsu | A61Q 11/00 424/49 |
| 5,766,574 A | 6/1998 | Christina-Beck et al. | |
| 6,713,049 B1 | 3/2004 | White et al. | |
| 2002/0155070 A1 | 10/2002 | Chen | |
| 2004/0208834 A1 * | 10/2004 | Koudate | A61K 8/8135 424/49 |
| 2006/0171907 A1 | 8/2006 | Scott et al. | |
| 2011/0152083 A1 | 6/2011 | Lu et al. | |

FOREIGN PATENT DOCUMENTS

| | | |
|---|---|---|
| JP | 2003/048842 A | 2/2003 |
| WO | WO 01/93820 A1 | 12/2001 |
| WO | WO 2007/111616 A1 | 10/2007 |

OTHER PUBLICATIONS

Database GNPD [Online] Mintel; Jan. 1, 2008, "Advanced Whitening Toothpaste" XP002729447, Database accession No. 845360.
Database GNPD [Online] Mintel Feb. 1, 2013, "Optic White Alcohol Free Mouthwash" XP002729448, Database accession No. 2006123.
Joiner et al., "Whitening toothpaste: A review of the literature", Journal of Dentistry, 2010, 38(1): e17-e24 (Abstract).
International Search Report for International Patent Application PCT/US2013/076887, provided by the International Search Authority, Date Mailed: Oct. 7, 2014.
SIPOMER® PAM-4000, Product Data Sheet n002195, Solvay Rhodia, 2012, Date Accessed: Aug. 23, 2016, (http://www.rhodia.com/product-literature-download.action?docId=0901663680d8e32e&docLanguage=EN&docType=TDS&output=BINARY&productName=Sipomer+PAM-4000).
Hoic et al., 2004, "The technology behind Colgate Simply White Toothpaste," J.Clinical Dentistry Professional Audience Communications 15(2):37-40.

* cited by examiner

*Primary Examiner* — Brian Gulledge

(57) ABSTRACT

Provided is an oral care composition comprising a phosphate/acrylate co-polymer, a whitening agent and an orally acceptable carrier and methods of using the same.

25 Claims, No Drawings

ORAL CARE COMPOSITIONS AND METHODS

BACKGROUND

Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

To combat staining and brighten or restore the natural enamel color, products containing bleaching materials are commercially available for professional and consumer use. The most commonly accepted chemicals used in teeth whitening today are peroxides. Peroxides are generally deemed safe from a physiological standpoint, and can be effective to whiten teeth. Such peroxides include hydrogen peroxide, carbamide peroxide, sodium perborate, and sodium percarbonate. When these peroxides are in appropriate contact with teeth they will usually oxidize stains, rendering the teeth whiter.

Professional dental treatments frequently include a tooth surface preparation such as acid etching followed by the application of highly concentrated bleaching solutions (e.g. up to 37% hydrogen peroxide) and/or the application of heat or light. (See, e.g., U.S. Pat. Nos. 5,425,953 and 5,766,574.) These procedures provide rapid results, but are expensive, and often require several trips to the dentist. In many cases, the patient's lips are uncomfortably retracted during the entire treatment and the patient is confined to sitting in the dental chair.

Alternatively, at home bleaching systems can be used. These systems have gained significant popularity in the past decade because of reduced cost, and increased convenience.

Current home treatment methods include abrasive toothpastes, toothpastes that produce oxides, whitening gels for use with a dental tray and whitening strips. The effectiveness of such techniques depends on a variety of factors including the type and intensity of the stain, the type of bleaching agent, contact time of the bleaching agent on the teeth, the amount of available bleaching active in the composition the ability of the bleaching agent to penetrate the tooth enamel, and consumer compliance. Effectiveness is also dependent on the amount of bleaching active in the composition, the ability of the active to be released during use, and the stability of the active in the product. However, the effectiveness of many of these treatments is adversely affected because of deficiencies in one or more factors relating to the composition and consumer compliance.

Biofilms form when bacteria adhere to surfaces in some form of watery environment and begin to excrete a slimy, glue-like substance that can stick to all kinds of materials—metals, plastics, soil particles, medical implant materials, biological tissues. Biofilms can be formed by a single bacterial species, but biofilms more often consist of many species of bacteria, as well as fungi, algae, protozoa, debris, and corrosion products. Essentially, a biofilm may form on any surface exposed to bacteria and some amount of water. Dental plaque is a yellowish biofilm that builds up on the teeth. Biofilms contain communities of disease-causing bacteria and their uncontrolled accumulation has been associated with cavities and gum disease (both gingivitis and periodontitis).

There is thus a need for novel oral compositions and methods that may inhibit staining and/or biofilm formation.

BRIEF SUMMARY

Provided herein is an oral care composition, and in particular a mouthwash composition, comprising a phosphate/acrylate co-polymer, a whitening agent, and an orally acceptable carrier.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, an "oral care composition" refers to a composition for which the intended use can include oral care, oral hygiene, or oral appearance, or for which the intended method of use can comprise administration to the oral cavity. In some embodiments, an oral care composition is not intentionally swallowed, but is rather retained in the oral cavity for a time sufficient to effect the intended utility. The oral care compositions as disclosed herein may be used in nonhuman mammals such as companion animals (e.g., dogs and cats), as well as by humans. In some embodiments, the oral care compositions as disclosed herein are used by humans.

As used herein, "phosphate/acrylate co-polymer" refers to a polymer made up of acrylate monomers and phosphatebearing monomers, e.g., a co-polymerized product of a mixture of acrylic acid, methacrylic acid, and 2-hydroxyethyl methacrylate phosphates of Formula 1:

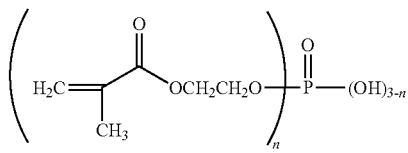

wherein n is 0, 1 or 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 70-90%, 80-90%, or about 85%; methacrylic acid in a molar percentage of 5-20%, 5-15%, or about 11%, and hydroxyethyl methacrylate phosphates of Formula 1 in a molar percentage of 1-10%, 2-6%, or about 4%. In some embodiments, the phosphate/acrylate co-polymer has a weight average molecular weight of from 10 to 500 kDa, optionally, 10 to 200 kDa, 10 to 40 kDa, 15 to 25, or 17 to 23 kDa, and the phosphate/acrylate co-polymer is below its glass transition temperature. In certain embodiments, the weight average molecular weight is 10 to 40 kDa. In other embodiments, the weight average molecular weight is 17 to 23 kDa. For example, in a particular embodiment, the phosphate/acrylate copolymer is a random copolymer that is the copolymerized product of a mixture of, in the relative amounts set forth in Table 1 below, 2-hydroxyethy methacrylate phosphates, acrylic acid, and methacrylic acid.

TABLE 1

| Monomer Name and Structure | Monomer Weight Ratio (weight %) | Monomer Molar Ratio (Mole %) |
|---|---|---|
| 2-hydroxyethyl methacylate phosphates<br>mixture of n = 0, n = 1, and n = 2 | 11 | 4 |
| acrylic acid | 75 | 85 |
| methacrylic acid | 14 | 11 |

Phosphate/acrylate co-polymers as described include DV8801 (Rhodia).

As used herein, the term "whitening agent" refers to an agent that whitens a tooth to which it is applied. The oral care compositions disclosed herein, comprise a whitening agent. In some embodiments, the oral care compositions disclosed herein comprise a whitening agent in a dental surface-whitening effective amount, e.g., 0.1 to 90 weight % whitening agent, e.g., 0.5 to 50 weight % whitening agent, e.g., 0.1 to 30 weight % whitening agent, e.g., 0.1 to 10 weight % whitening agent, e.g., 0.1 to 5 weight % whitening agent, e.g., 0.1 to 4 weight % whitening agent, e.g., 0.1 to 3 weight % whitening agent, e.g., 2 weight % whitening agent. Examples of whitening agents that may be used in the oral compositions disclosed herein include, for example, peroxides, metal chlorites, perborates, percarbonates, peroxyacids, hypochlorites, and mixtures thereof. In some embodiments, the whitening agent is hydrogen peroxide or a hydrogen peroxide source, for example, urea peroxide or a peroxide salt or complex (for example, peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or a hydrogen peroxide polymer complex (for example, a peroxide-polyvinyl pyrrolidone polymer complex). In some preferred embodiments, the whitening agent is hydrogen peroxide.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers can include, for example, one or more of the following: water, a buffer, a humectant, a surfactant, a sweetener, a flavorant, a pigment, a dye, an anti-caries agent, an anti-bacterial, a whitening agent, a desensitizing agent, a vitamin, a preservative, an enzyme, and mixtures thereof. In some preferred embodiments, the orally acceptable carrier is a mixture of one or more of water, a sugar alcohol such as sorbitol, and propylene glycol.

As used herein, a "tartar control agent" refers to a compound or a mixture of compounds that inhibit the formation of tartar, a mixture of calcium phosphates on organic matrices, and/or the deposition of plaque on teeth to form tartar (calculus). Representative tartar control agents include polyphosphate compounds, for example and not limitation polyphosphate salts such as metal hexametaphosphate salts, for example and not limitation sodium hexametaphosphate, tripolyphosphate salts, for example and not limitation sodium tripolyphosphate, and pyrophosphate salts, for example and not limitation sodium acid pyrophosphate.

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a denture, dental plate, crown, cap, filling, bridge, dental implant and the like. In some embodiments, the dental surface is a natural tooth.

The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. The co-polymer may also prevent bacteria from sticking together.

The present invention provides mouthwash compositions that contain levels of whitening agent, for example hydrogen peroxide, that provide effective tooth whitening, and also contain a phosphate/acrylate co-polymer that can reduce staining and calculus build-up on teeth, thus further enhancing whitening.

Most ingredients which can provide the benefits of stain reduction or calculus prevention are incompatible with whitening agents such as hydrogen peroxide, either because they directly destabilize the peroxide, or because they are unstable or ineffective in the pH range that hydrogen peroxide is stable. Moreover, even a small amount of hydrogen peroxide degradation results in gas production, which results in observable bloating of the product in a deformable bottle such as commonly used for mouthwash. Although the level of hydrogen peroxide may still be effective for tooth whitening, the physical appearance of the product is no longer consumer acceptable and is perceived as unstable. In contrast, the compositions of the present invention provide a suitable level of hydrogen peroxide for tooth whitening (for example, greater or equal to 1.5%) and also a phosphate/acrylate co-polymer that can reduce staining and calculus build-up on teeth. In some embodiments, the compositions can additionally include one or more polymeric phosphate salts, which are both stable and effective in a pH range of 3.0-5.5, and do not negatively impact the stability of hydrogen peroxide, such as, for example, metal hexametaphosphate salts such as sodium hexametaphosphate, tripolyphosphate salts such as sodium tripolyphosphate, and pyrophosphate salts, such as sodium acid pyrophosphate.

Accordingly, provided herein is an oral care composition (Composition 1) comprising a phosphate/acrylate co-polymer, a whitening agent, and an orally acceptable carrier.

Further provided herein is Composition 1 as follows:
1.1 Composition 1 wherein the composition comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 phosphate/acrylate co-polymer, e.g., e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight % phosphate/acrylate co-polymer, e.g., 1 to 8 weight % phosphate/acrylate co-polymer, e.g., 1 to 6 weight % phosphate/acrylate co-polymer, e.g., 1 to 5 weight % phosphate/acrylate co-polymer, e.g., 1 to 4 weight % phosphate/acrylate co-polymer, e.g., 1 to 3 weight % phosphate/acrylate co-polymer, e.g., 2 to 3 weight % phosphate/acrylate co-polymer.
1.2 Any foregoing composition wherein the phosphate/acrylate co-polymer is a co-polymerized product of a mixture of acrylic acid, methacrylic acid, and 2-hydroxyethyl methacrylate phosphates of Formula 1:

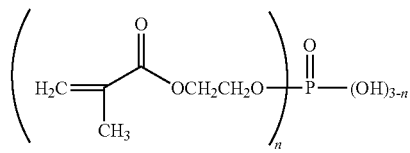

wherein n is 0, 1 or 2.

1.3 Any foregoing composition wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.
1.4 Any foregoing composition wherein the phosphate/acrylate co-polymer has an average molecular weight of from 10 to 40 kDa, e.g., 20 to 30 kDa; or from 30 to 50 kDa. e.g., 40 kDa; or from 90 to 110 kDa, e.g. 98 kDa; or from 100 to 120 kDa, e.g., 109 kDa; or from 120 to 140 kDa, e.g. 131 kDa; or from 185 to 205 kDa, e.g., 195 kDa.
1.5 Any foregoing composition wherein the phosphate/acrylate copolymer is a random copolymer having a weight average molecular weight of about 20,000 to 30,000 grams per mole or 35,000 to 45,000 grams per mole that is the copolymerized product of a mixture of acrylic acid, methacrylic acid, and 2-hydroxyethy methacrylate phosphates of Formula 1, e.g., in a molar ratio of about 85:11:4.
1.6 Any foregoing composition wherein the whitening agent is hydrogen peroxide, in a dental surface-whitening effective amount, e.g., 0.1 to 90 weight % hydrogen peroxide, e.g., 0.5 to 50 weight % hydrogen peroxide. e.g., 0.1 to 30 weight % hydrogen peroxide, e.g., 0.1 to 10 weight % hydrogen peroxide, e.g., 0.1 to 5 weight % hydrogen peroxide. e.g., 0.1 to 4 weight % hydrogen peroxide, e.g., 0.1 to 3 weight % hydrogen peroxide, e.g., 2 weight % hydrogen peroxide.
1.7 Any foregoing composition wherein the composition comprises an anti-tartar agent.
1.8 Composition 1.7, wherein the anti-tartar agent is a polyphosphate salt.
1.9 Composition 1.8, wherein the polyphosphate salt is a metal hexametaphosphate salt, sodium hexametaphosphate, a tripolyphosphate salt, sodium tripolyphosphate, a pyrophosphate salts, or sodium acid pyrophosphate.
1.10 Composition 1.8, wherein the polyphosphate salt is sodium hexametaphosphate.
1.11 Any foregoing composition wherein the composition comprises one or more surfactants, one or more detergents, one or more emulsifiers, or any combination thereof.
1.12 Composition 1.11, wherein the surfactants, detergents and emulsifiers are selected from poloxamers and polysorbates.
1.13 Composition 1.11, wherein the surfactants, detergents and emulsifiers are selected from poloxamer 407 and polysorbate 20.
1.14 Any foregoing composition wherein the composition comprises one or more agents selected from antibacterial agents and antiseptic agents.
1.15 Composition 1.14 wherein the anti-bacterial and/or antiseptic agents comprise menthol, methyl salicylate, or a combination thereof.
1.16 Composition 1.14 or 1.15 wherein the anti-bacterial agent is triclosan, cetylpyridinium chloride (CPC), chlorhexidine (CHX), stannous salts, essential oils, water soluble zinc salts, water insoluble zinc salts, e.g., ZnO or zinc citrate, or a mixture thereof, e.g., wherein the anti-bacterial agent is triclosan, e.g., wherein the anti-bacterial agent is ZnO, e.g., wherein the antibacterial agent is zinc citrate, e.g., wherein the antibacterial agent is a mixture thereof.

1.17 Any foregoing composition wherein the orally acceptable carrier comprises water and humectant selected from one or more of a sugar alcohol, an alkylene glycol, glycerin, or combination thereof.

1.18 Composition 1.17, wherein the orally acceptable carrier comprises water, sorbitol and propylene glycol; for example water in an amount of from 1% to 90%; and for example sorbitol (70%) in an amount of from 0.1% to 8%, for example 0.1% to 1%, for example 0.5%; and for example propylene glycol in an amount of from 5% to 10%, for example 7%.

1.19 Any foregoing composition wherein the composition comprises a sweetener.

1.20 Composition 1.19 wherein the sweetener is sodium saccharin.

1.21 Any foregoing composition wherein the composition comprises a flavorant.

1.22 Any foregoing composition wherein the composition comprises a pigment.

1.23 Any foregoing composition wherein the composition comprises:
phosphate/acrylate co-polymer in an amount of from 0.1% to 5%;
hydrogen peroxide in an amount of from 0.01% to 4%; and
one or more polyphosphate salts in an aggregate amount of from 0.1% to 3%.

1.24 Composition 1.23, wherein:
the phosphate/acrylate co-polymer is DV8801; and
the polyphosphate salts comprise sodium hexametaphosphate.

1.25 Any foregoing composition wherein the composition comprises a desensitizing agent, a vitamin, a preservative, an enzyme, or a mixture thereof.

In some embodiments, the oral care compositions disclosed herein, e.g., Composition 1, e.g., 1.1-1.24, comprise one or more detergents or surfactants, e.g., selected from anionic, cationic, zwitterionic, and nonionic surfactants, and mixtures thereof. In some embodiments, the surfactant is reasonably stable throughout a wide pH range. Surfactants are described in, for example, U.S. Pat. No. 3,959,458, to Agricola et al; U.S. Pat. No. 3,937,807, to Haefele; and U.S. Pat. No. 4,051,234, to Gieske et al. In some embodiments, the oral care compositions disclosed herein, e.g., Composition 1, e.g., 1.1-1.24, comprise from 0.01 to 10 weight % of a surfactant, e.g., 0.05 to 5 weight % of a surfactant, e.g., 0.1 to 10 weight % of a surfactant, e.g., 0.1 to 5 weight % of a surfactant, e.g., 0.1 to 2 weight % of a surfactant, e.g., 0.5 to 2 weight % of a surfactant. In some embodiments, the oral care compositions disclosed herein, e.g., Composition 1, e.g., 1.1-1.24, comprise from 0.01 to 10 weight % of one or more nonionic surfactants, e.g., 0.05 to 5 weight % of nonionic surfactant, e.g., 0.1 to 10 weight % of nonionic surfactant, e.g., 0.1 to 5 weight % of nonionic surfactant, e.g., 0.1 to 2 weight % of nonionic surfactant, e.g., 0.5 to 2 weight % of nonionic surfactant, e.g., 1 weight % of nonionic surfactant. In some embodiments, the surfactant or surfactants, for example nonionic surfactant or surfactants, can also function as an emulsifier. Preferred examples of surfactants for use in the present invention include polysorbates and poloxamers, for example polysorbate 20 and poloxamer 407. In some embodiments, the compositions of the invention include polysorbate 20 in an amount of from 0.1 to 5 weight %; for example from 0.1 to 2 weight %; for example from 0.1 to 1 weight %; for example 0.5 weight %.

In some embodiments, the compositions of the invention include poloxamer 407 in an amount of from 0.1 to 5 weight %; for example from 0.1 to 2 weight %; for example 1 weight %. In some embodiments, the compositions of the invention include both polysorbate 20 and poloxamer 407, for example in the foregoing amounts.

In some embodiments, the oral care compositions disclosed herein, e.g., Composition 1, e.g., 1.1-1.24, comprise one or more anti-bacterial or antiseptic agents. In some embodiments, the oral care compositions disclosed herein, e.g., Composition 1, e.g., 1.1-1.24, comprise 0.01 to 10 weight %; e.g., 0.1 to 10 weight %; e.g., 0.5 to 5 weight %; e.g., 0.01 to 5 weight %; e.g., 0.05 to 4 weight %; e.g., 0.05 to 3 weight %; e.g., 0.05 to 2 weight %; e.g., 0.05 to 1 weight %; e.g., 0.1 to 1 weight %; e.g., 0.1 to 0.5 weight % of one or more anti-bacterial and/or antiseptic agents. Examples of anti-bacterial and antiseptic agents that may be used in the oral compositions disclosed herein, e.g., Composition 1, e.g., 1.1-1.24, include, for example, halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts, and mixtures thereof. In some embodiments, the anti-bacterial and antiseptic agents are selected from menthol and methyl salicylate. In some such embodiments, the oral care compositions disclosed herein, e.g., Composition 1, e.g., 1.1-1.24, comprise menthol and methyl salicylate, each in an in an amount of from 0.01 to 10 weight %; e.g., 0.01 to 5 weight %; e.g., 0.05 to 4 weight %; e.g., 0.05 to 3 weight %; e.g., 0.05 to 2 weight %; e.g., 0.05 to 1 weight %; e.g., 0.1 weight %.

The orally acceptable carriers of the invention can include water, and one or more humectants, which function, inter alia, to keep the oral cavity moist after application of the mouthwash. Certain humectants can also impart desirable sweetness or flavor to oral care compositions. In some embodiments, the oral care compositions disclosed herein, e.g., Composition 1, e.g., 1.1-1.24, comprise, on a pure humectant basis, from 0 to 70 weight % of humectant, e.g., 10 to 70 weight % of humectant, e.g., 10 to 65 weight % of humectant, e.g., 10 to 60 weight % of humectant. e.g., 10 to 50 weight % of humectant, e.g., 10 to 30 weight % of humectant, e.g., 20 to 50 weight % of humectant, e.g., 20 to 40 weight % of humectant. Humectants that may be used in the oral care compositions disclosed herein, e.g., Composition 1, e.g., 1.1-1.24, include, for example, one or more of glycerin, sorbitol, xylitol, butylene glycol, polyethylene glycol, propylene glycol, trimethyl glycine, and mixtures thereof. In some embodiments, e.g., Composition 1, e.g., 1.1-1.24, the humectants include sorbitol, propylene glycol and mixtures thereof. In some such embodiments, the oral care compositions disclosed herein, e.g., Composition 1, e.g., 1.1-1.24, comprise, on a pure humectant basis, from 0 to 20 weight % of sorbitol and propylene glycol, e.g., 5 to 10 weight % of sorbitol and propylene glycol, e.g., 7 to 8 weight % of sorbitol and propylene glycol. In some embodiments, the mixture of sorbitol and propylene glycol contains from 0.1 to 2 weight % sorbitol (70%), for example 0.5% sorbitol (70%); and from 5 to 10 weight % propylene glycol, for example from 6 to 8 weight % propylene glycol, for example 7% propylene glycol.

In some embodiments, the oral care compositions disclosed herein, e.g., Composition 1, e.g., 1.1-1.24, comprise water, for example but not limitation as a component of the orally acceptable carrier. Water employed in the preparation of the oral care compositions disclosed herein, e.g., Composition 1, e.g., 1.1-1.24, should be deionized and free of organic impurities. Water may make up the balance of the oral care composition. In some embodiments, the oral care compositions disclosed herein, e.g., Composition 1, e.g., 1.1-1.24, comprise 0 to 90 weight % water, e.g., 0.1 to 90 weight % water, e.g., 1 to 80 weight % water, e.g., 2 to 70 weight % water, 5 to 60 weight % water, e.g., 5 to 50 weight % water, e.g., 20 to 60 weight % water, e.g., 10 to 40 weight % water. This amount of water includes the free water which is added plus that amount which is introduced with other components of the oral care composition, such as with sorbitol.

In some embodiments, the oral care compositions disclosed herein, e.g., Composition 1, e.g., 1.1-1.24, comprise a sweetener. In some embodiments, the oral care compositions disclosed herein, e.g., Composition 1, e.g., 1.1-1.24, comprise 0.005 to 10 weight % of a sweetener, e.g., 0.01 to 10 weight % of a sweetener, e.g., 0.1 to 10 weight % of a sweetener, e.g., from 0.1 to 5 weight % of a sweetener, e.g., from 0.1 to 3 weight % of a sweetener. e.g., from 0.1 to 1 weight % of a sweetener, e.g., from 0.1 to 0.5 weight % of a sweetener. Sweeteners that may be used in the oral care compositions disclosed herein, e.g., Composition 1. e.g., 1.1-1.24, include, for example, sucrose, glucose, saccharin, sucralose, dextrose, levulose, lactose, mannitol, sorbitol, fructose, maltose, xylitol, saccharin salts (e.g., sodium saccharin), thaumatin, aspartame, D-tryptophan, dihydrochalcones, acesulfame, cyclamate salts, and mixtures thereof. In some embodiments, sodium saccharin is used as the sweetener in the oral care compositions disclosed herein, e.g., Composition 1, e.g., 1.1-1.24. In some embodiments, the oral care compositions disclosed herein, e.g., Composition 1, e.g., 1.1-1.24, comprise 0.005 to 10 weight % sodium saccharin, e.g., 0.01 to 1 weight % sodium saccharin, e.g., 0.01 to 0.5 weight % sodium saccharin, e.g., from 0.01 to 0.05 weight % sodium saccharin, e.g., 0.04 weight % sodium saccharin.

In some embodiments, the oral care compositions disclosed herein, e.g., Composition 1, e.g., 1.1-1.24, comprise a flavorant. In some embodiments, the oral care compositions disclosed herein, e.g., Composition 1, e.g., 1.1-1.24, comprise 0.01 to 5 weight % of a flavorant, e.g., 0.01 to 4 weight % of a flavorant, e.g., 0.01 to 3 weight % of a flavorant, e.g., 0.01 to 2 weight % of a flavorant, e.g., 0.05 to 0.5 weight % of a flavorant, e.g., 0.05 to 0.15 weight % of a flavorant, e.g., 0.05 to 2 weight % of a flavorant, e.g., 0.5 to 2 weight % of a flavorant, e.g., 0.7 to 2 weight % of a flavorant, e.g., 0.8 to 2 weight % of a flavorant e.g., 0.9 to 2 weight % of a flavorant, e.g., 1 to 2 weight % of a flavorant. Flavorants that may be used in the oral care compositions disclosed herein, e.g., Composition 1, e.g., 1.1-1.24, include, for example, essential oils, as well as various flavoring aldehydes, esters, alcohols, and similar materials, as well as menthol, carvone, and anethole, as well as mixtures thereof. Examples of essential oils include oils of spearmint, peppermint, wintergreen, *sassafras*, clove, sage, *eucalyptus*, marjoram, cinnamon, lemon, lime, grapefruit, and orange. In some embodiments, a mixture of wintergreen (methyl salicylate) and menthol is used as the flavorant in the oral care compositions disclosed herein, e.g., Composition 1. e.g., 1.1-1.24, for example in an amount of from 0.01 to 0.2 weight %, for example 0.1 weight % each. It will be appreciated that the methyl salicylate and menthol can also function as antiseptic and/or antibacterial in the oral care compositions disclosed herein, e.g., Composition 1, e.g., 1.1-1.24.

A buffer can optionally be used to adjust the pH of oral care compositions. In some embodiments, the oral care compositions disclosed herein, e.g., Composition 1, e.g., 1.1-1.24, comprise from 0.1 to 10 weight % of a buffer, 0.5 to 10 weight % of a buffer, e.g., 0.5 to 5 weight % of a buffer, e.g., 0.5 to 4 weight % of a buffer, e.g., 0.5 to 3 weight % of a buffer, e.g., 0.5 to 2 weight % of a buffer, e.g., 1 to 2 weight % of a buffer. Buffers that may be used in the oral care compositions disclosed herein, e.g., Composition 1, e.g., 1.1-1.24, include, for example, sodium bicarbonate, sodium phosphate {e.g., monosodium phosphate ($NaH_2PO_4$), disodium phosphate ($Na_2HPO_4$), trisodium phosphate ($Na_3PO_4$)}, sodium hydroxide, sodium carbonate, sodium acid pyrophosphate, citric acid, sodium citrate, and mixtures thereof. In some embodiments, sodium hydroxide is used as the buffer in the oral care compositions disclosed herein, e.g., Composition 1, e.g., 1.1-1.24. In some embodiments, the oral care compositions disclosed herein, e.g., Composition 1, e.g., 1.1-1.24, comprise from 0.1 to 10 weight % of phosphoric acid. e.g., 0.5 to 10 weight % of phosphoric acid, e.g., 0.5 to 5 weight % of phosphoric acid, e.g., 0.5 to 4 weight % of phosphoric acid, e.g., 0.5 to 3 weight % of phosphoric acid, e.g., 0.5 to 2 weight % of phosphoric acid, e.g., 1 to 2 weight % of phosphoric acid.

In some embodiments, the oral care compositions disclosed herein, e.g., Composition 1, e.g., 1.1-1.24, further comprise an anti-caries agent. In some embodiments, the oral care compositions disclosed herein, e.g., Composition 1, e.g., 1.1-1.24, comprise 0.005 to 10 weight % of the anti-caries agent, e.g., 0.01 to 10 weight % of the anti-caries agent, e.g., 0.01 to 5 weight % of the anti-caries agent, e.g., 0.01 to 1 weight % of the anti-caries agent, e.g., 0.01 to 0.3 weight % of the anti-caries agent, e.g., 0.1 to 10 weight % of the anti-caries agent, e.g., 0.1 to 5 weight % of the anti-caries agent, e.g., 0.1 to 2 weight % of the anti-caries agent, e.g., 0.1 to 1 weight % of the anti-caries agent, e.g., 0.1 to 0.8 weight % of the anti-caries agent, e.g., 0.1 to 0.6 weight % of the anti-caries agent, e.g., 0.1 to 0.5 weight % of the anti-caries agent. In some embodiments, the anti-caries agent is a fluoride ion source. In some embodiments, the oral care compositions disclosed herein, e.g., Composition 1, e.g., 1.1-1.24, further comprise 0.005 to 10 weight % of the anti-caries agent which is a fluoride ion source, e.g., 0.01 to 10 weight % of the anti-caries agent which is a fluoride ion source, e.g., 0.01 to 5 weight % of the anti-caries agent which is a fluoride ion source, e.g., 0.01 to 1 weight % of the anti-caries agent which is a fluoride ion source, e.g., 0.01 to 0.3 weight % of the anti-caries agent which is a fluoride ion source, e.g., 0.1 to 10 weight % of the anti-caries agent which is a fluoride ion source, e.g., 0.1 to 5 weight % of the anti-caries agent which is a fluoride ion source, e.g., 0.1 to 2 weight % of the anti-caries agent which is a fluoride ion source, e.g., 0.1 to 1 weight % of the anti-caries agent which is a fluoride ion source, e.g., 0.1 to 0.8 weight % of the anti-caries agent which is a fluoride ion source, e.g., 0.1 to 0.6 weight % of the anti-caries agent which is a fluoride ion source, e.g., 0.1 to 0.5 weight % of the anti-caries agent which is a fluoride ion source. Examples of fluoride ion sources that may be used in the oral compositions disclosed herein, e.g., Composition 1, e.g., 1.1-1.24, are found in U.S. Pat. No. 3,535,421 to Briner et al.; U.S. Pat. No. 4,885,155 to Parran, Jr. et al., and U.S. Pat. No. 3,678,154 to Widder et al. Other examples of fluoride ion sources include, for example, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof. In certain embodiments the fluoride ion source includes stannous fluoride, sodium fluoride, and sodium monofluorophosphate, as well as mixtures thereof. In some embodiments, the anti-caries agent is sodium fluoride. In some embodiments, the oral care compositions disclosed herein, e.g., Composition 1, e.g., 1.1-1.24, comprise 0.005 to 10 weight % sodium fluoride, e.g., 0.01 to 10 weight % sodium fluoride, e.g., 0.01 to 5 weight % sodium fluoride, e.g., 0.01 to 1 weight % sodium fluoride, e.g., 0.01 to 0.3 weight % sodium fluoride, e.g., 0.1 to 10 weight % sodium fluoride, e.g., 0.1 to 5 weight % sodium fluoride, e.g., 0.1 to 2 weight % sodium fluoride, e.g., 0.1 to 1 weight % sodium fluoride, e.g., 0.1 to 0.8 weight % sodium fluoride, e.g., 0.1 to 0.6 weight % sodium fluoride, e.g., 0.1 to 0.5 weight % sodium fluoride.

In some embodiments, the oral care compositions disclosed herein, e.g., Composition 1, e.g., 1.1-1.24, comprise the anti-caries agent which is a fluoride ion source in an amount sufficient to supply 25 ppm to 25,000 ppm of fluoride ions, e.g., from 100 to 20,000 ppm of fluoride ions, e.g., from 300 to 15.000 ppm of fluoride ions, e.g., from 500 to 10.000 ppm of fluoride ions, e.g., from 500 to 8,000 ppm of fluoride ions, e.g., from 500 to 6,000 ppm of fluoride ions, e.g., from 500 to 4,000 ppm of fluoride ions, e.g., from 500 to 2,000 ppm of fluoride ions, e.g., from 500 to 1,800 ppm of fluoride ions, e.g., from 1000 to 1600 ppm, e.g., 1450 ppm of fluoride ions. The appropriate level of fluoride ions will depend on the particular application. In some embodiments, a toothpaste for consumer use comprises the anti-caries agent which is a fluoride ion source in an amount sufficient to supply from 1,000 to 1,500 ppm of fluoride ions, with pediatric toothpaste having somewhat less. In some embodiments, a dentifrice or coating for professional application comprises the anti-caries agent which is a fluoride ion source in an amount sufficient to supply from 5,000 to 25.000 ppm of fluoride ions.

The compositions of the invention can also contain one or more pigments or colorants known in the art to provide color to the mouthwash composition. Examples of suitable pigments or colorants include dyes such as FDC Red 40, FDC Green 3, FDC Brown mixture, FDC Yellow 5, DC Red 19, DC Red 33, DC Yellow 10, and the like, for example in an amount of from 0.01-0.2 weight %.

As will be evident to one of skill in the art, some components of the invention may perform multiple functions, and the identification of a compound as having one function herein is not meant to exclude its use for other functions in a particular composition. For example, a compound such as menthol can act both as a flavorant and an antiseptic agent; a compound such as polysorbate 20 can act as both a surfactant and as an emulsifier; a compound such as hydrogen peroxide can act as both a whitening agent and an antibacterial agent; and a compounds such as sodium hexametaphosphate can act as both an anti-stain agent, and a tartar preventing agent.

In some embodiments, an oral care composition disclosed herein comprises:

| Ingredient | % |
| --- | --- |
| Propylene Glycol | 7 |
| Menthol | 0.1 |
| Methyl Salicylate | 0.1 |
| Poloxomer 407 | 1 |
| Sodium Saccharin | 0.04 |
| NC Sorbitol (70%) | 0.5 |
| Polysorbate 20 | 0.5 |
| Phosphate/acrylate polymer; e.g., DV8801 Polymer (40%) | 0.100-5; e.g., 2.5 |
| Sodium Hexametaphosphate | 0.5 |
| Hydrogen Peroxide* | 0.1-5; e.g., 1-3; e.g., 2 |
| Phosphoric acid (85%) | QS to pH 5 |
| Water | Balance |

*For example, 5.7143% of a 35% solution to yield 2% in final composition.

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:
A.1 Method A wherein the composition is Composition 1, e.g., 1.1-1.24.
A.2 Method A or A.1 wherein the method is for the treatment of a chemical stain, plaque, acid erosion, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of acid erosion on the dental surface.
A.6 Method A.2 wherein the method is for the treatment of tartar on the dental surface.
A.7 Method A or A.1 wherein the method is for the inhibition of a chemical stain, plaque, and/or tartar on the dental surface.
A.8 Method A.7 wherein the method is for the inhibition of a chemical stain on the dental surface.
A.9 Method A.7 wherein the method is for the inhibition of plaque on the dental surface.
A.10 Method A.7 wherein the method is for the inhibition of acid erosion on the dental surface.
A.11 Method A.7 wherein the method is for the inhibition of tartar on the dental surface.
A.12 Method A or A.1-A.11 wherein the dental surface is a human tooth.
A.13 Method A or A.1-A.12 wherein the composition is contacted with the dental surface by brushing.

Further provided is a method (Method B) for the treatment and/or inhibition of gum disease comprising contacting the oral cavity with any of the preceding oral care compositions.

Further provided herein is Method B as follows:
B.1 Method B wherein the composition is Composition 1, e.g., 1.1-1.24.
B.2 Method B or B.1 wherein the method is for the treatment of gum disease.
B.3 Method B, B.1, or B.2 wherein the gum disease is gingivitis.

B.4 Method B, B.1, or B wherein the gum disease is periodontitis.

B.5 Method B or B.1 wherein the method is for the inhibition of gum disease.

B.6 Method B, B.1, or B.5 wherein the gum disease is gingivitis.

B.7 Method B, B.1, or B.5 wherein the gum disease is periodontitis.

B.8 Method B or B.1-B.7 wherein the oral cavity is a human oral cavity.

B.9 Method B or B.1-B.8 wherein the composition is contacted with the oral cavity by rinsing.

Further provided is a method (Method C) for the treatment and/or inhibition of halitosis comprising contacting the oral cavity with any of the preceding oral care compositions.

Further provided herein is Method C as follows:

C.1 Method C wherein the composition is Composition 1, e.g., 1.1-1.24.

C.2 Method C or C.1 wherein the oral cavity is a human oral cavity.

C.3 Method C, C.1, or C.2 wherein the composition is contacted with the oral cavity by rinsing.

Further provided is a method (Method D) for inhibiting biofilm formation on a dental surface comprising contacting the dental surface with any of the preceding oral care compositions.

Further provided herein is Method D as follows:

D.1 Method D wherein the composition is Composition 1, e.g., 1.1-1.24.

D.2 Method D or D.1 wherein the dental surface is a human tooth.

D.3 Method D, D.1, or D.2 wherein the composition is contacted with the dental surface by rinsing.

Further provided is a use (Use A) of any of the preceding oral care compositions for the treatment and/or inhibition of a chemical stain, plaque, and/or tartar on a dental surface comprising contacting the dental surface with any of the preceding oral care compositions.

Further provided herein is Use A as follows:

A.1 Use A wherein the composition is Composition 1, e.g., 1.1-1.24.

A.2 Use A or A.1 wherein the use is for the treatment of a chemical stain, plaque, acid erosion, and/or tartar on the dental surface.

A.3 Use A.2 wherein the use is for the treatment of a chemical stain on the dental surface.

A.4 Use A.2 wherein the use is for the treatment of plaque on the dental surface.

A.5 Use A2 wherein the use is for the treatment of acid erosion on the dental surface.

A.6 Use A.2 wherein the use is for the treatment of tartar on the dental surface.

A.7 Use A or A.1 wherein the use is for the inhibition of a chemical stain, plaque, acid erosion, and/or tartar on the dental surface.

A.8 Use A.7 wherein the use is for the inhibition of a chemical stain on the dental surface.

A.9 Use A.7 wherein the use is for the inhibition of plaque on the dental surface.

A.10 Use A.7 wherein the use is for the inhibition of acid erosion on the dental surface.

A.11 Use A.7 wherein the use is for the inhibition of tartar on the dental surface.

A.12 Use A or A.1-A.11 wherein the dental surface is a human tooth.

A.13 Use A or A.1-A.12 wherein the composition is contacted with the dental surface by brushing.

Further provided is a use (Use B) of any of the preceding oral care compositions for the treatment and/or inhibition of gum disease in an oral cavity comprising contacting the oral cavity with any of the preceding oral care compositions.

Further provided herein is Use B as follows:

B.1 Use B wherein the composition is Composition 1, e.g., 1.1-1.57.

B.2 Use B or B.1 wherein the use is for the treatment of gum disease.

B.3 Use B, B.1, or B.2 wherein the gum disease is gingivitis.

B.4 Use B, B.1, or B wherein the gum disease is periodontitis.

B.5 Use B or B.1 wherein the use is for the inhibition of gum disease.

B.6 Use B, B.1, or B.5 wherein the gum disease is gingivitis.

B.7 Use B, B.1 or B.5 wherein the gum disease is periodontitis.

B.8 Use B or B.1-B.7 wherein the oral cavity is a human oral cavity.

B.9 Use B or B.1-B.8 wherein the composition is contacted with the oral cavity by rinsing.

Further provided is a use (Use C) of any of the preceding oral care compositions for the treatment and/or inhibition of halitosis in an oral cavity comprising contacting the oral cavity with any of the preceding oral care compositions.

Further provided herein is Use C as follows:

C.1 Use C wherein the composition is Composition 1, e.g., 1.1-1.57.

C.2 Use C or C.1 wherein the oral cavity is a human oral cavity.

C.3 Use C, C.1, or C.2 wherein the composition is contacted with the oral cavity by rinsing.

Further provided is a use (Use D) of any of the preceding oral care compositions for the inhibition of biofilm formation on a dental surface comprising contacting the dental surface with any of the preceding oral care compositions.

Further provided herein is Use D as follows:

D.1 Use D wherein the composition is Composition 1, e.g., 1.1-1.57.

D.2 Use D or D.1 wherein the oral cavity is a human oral cavity.

D.3 Use D, D.1, or D.2 wherein the composition is contacted with the oral cavity by rinsing.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.10, and Use B, e.g., B.1-B.10, are effective to inhibit formation and development of new chemical stains, as can occur for example by oral use of tobacco products (including smoking) or by drinking tea or coffee, subsequent to treatment according to the method. Where the dental surface already possesses some degree of chemical staining, Method A, e.g., A.1-A.10, and Use B, e.g., B.1-B.10, are effective to inhibit further development of the existing stain. In some embodiments, the Method A, e.g., A.1-A.10, and Use B, e.g., B.11-B.10, can remove, partially or completely, an existing chemical stain as well as inhibit subsequent staining.

EXAMPLES

Example 1

Mouth Rinse Compositions

Mouth Rinse formulations were prepared containing 1) 2% hydrogen peroxide; 2) 2% hydrogen peroxide plus 1% phosphate/acrylate co-polymer (DV8801, MW 40,000); and 3) 2% hydrogen peroxide plus 1% phosphate/acrylate co-polymer (DV8801, MW 40,000), plus 0.5% sodium hexametaphosphate, as shown in Table 2 below.

TABLE 2

Mouth Rinse Formulations

| Material | 2.0% HP | 2.0% HP & 1% DV8801 Polymer | 2.0% HP & 1% DV8801 Polymer & 0.5% SHMP |
|---|---|---|---|
| Propylene Glycol | 7 | 7 | 7 |
| Menthol | 0.1 | 0.1 | 0.1 |
| Methyl Salicylate | 0.1 | 0.1 | 0.1 |
| Poloxomer 407 | 1 | 1 | 1 |
| Sodium Saccharin | 0.04 | 0.04 | 0.04 |
| NC Sorbitol (70%) | 0.5 | 0.5 | 0.5 |
| Polysorbate 20 | 0.5 | 0.5 | 0.5 |
| DV8801 Polymer (40%) | — | 2.5 | 2.5 |
| Sodium Hexametaphosphate | — | — | 0.5 |
| Hydrogen Peroxide (35%) | 5.7143 | 5.7143 | 5.7143 |
| Phosphoric Acid (85%) | QS to pH 5 | QS to pH 5 | QS to pH 5 |
| Water | Balance | Balance | Balance |

The mouth rinse formulations were analyzed for both hydrogen peroxide stability, and stain prevention efficacy using the The in vitro stain inhibition test of Example 2 below.

Example 2

In Vitro Stain Inhibition Test

The in vitro stain inhibition test is conducted on hydroxyapatite disc (HAP disc) and the efficacy is quantified by measuring the light reflected from the surface of HAP disc after treatment with the mouth rinse and subsequent exposure to a staining agent, in this case, coffee. The measurement is taken with a chromameter and L*a*b* value recorded. The HAP disc is first soaked in saliva overnight and baseline whiteness is measured, next it is treated with the mouth rinse of Example 1 for 5 minutes and the initial L*a*b* is recorded right away. After that, the HAP disc is exposed to a coffee stain for 15 minutes, rinsed with distilled ionized water and incubated in saliva for 20 minutes. The above staining process is repeated a total three times and the final L*a*b* is read again which would compare to initial L*a*b* to show how well the dentifrice could prevent the coffee stain from forming on the HAP disc. The less the delta L*, the better stain prevention effect provided by the dentifrice.

Results of Stability and Stain Prevention Tests

The test results are shown in Table 3 below.

TABLE 3

Results of Stability and Stain Prevention Tests

| Formula | Hydrogen Peroxide Degradation (3 mo@40° C./75% RH) | Stain Prevention Efficacy (ΔL*) |
|---|---|---|
| 2% HP | −0.04% (−1.88% change) | 35.5 |
| 2% HP + 1% DV8801 | −0.06% (−2.82% change) | 7.1 |
| 2% HP + 1% DV8801 + 0.5% SHMP | −0.08% (−3.76% change) | 4.4 |

The hydrogen peroxide stability of the formulation containing 1% DV8801 polymer is substantially similar to that of the formula without the polymer, however the stain prevention benefit of the polymer is significant. Further addition of sodium hexametaphosphate provides an incremental increase in stain prevention efficacy, while still maintaining greater than 95% of the hydrogen peroxide after 3 months aging at 40° C./75% relative humidity.

What is claimed is:

1. An oral care composition comprising a phosphate/acrylate co-polymer, a whitening agent, and an orally acceptable carrier, wherein the phosphate/acrylate co-polymer is a co-polymerized product of a mixture of acrylic acid, methacrylic acid, and a mixture of 2-hydroxyethyl methacrylate phosphates of Formula 1:

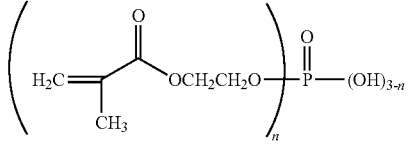

wherein n is 0, 1 or 2.

2. The composition of claim 1, wherein the composition comprises 0.1 weight % to 10 weight % of the phosphate/acrylate co-polymer.

3. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 70-90%; methacrylic acid in a molar percentage of 5-20%, and hydroxyethyl methacrylate phosphates of Formula 1 in a molar percentage of 1-10%.

4. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90% or 85%; methacrylic acid in a molar percentage of 5-15% or 11%, and hydroxyethyl methacrylate phosphates of Formula 1 in a molar percentage of 2-6% or 4%.

5. The composition of claim 1, wherein the phosphate/acrylate copolymer is a random copolymer having a weight average molecular weight of 10,000 to 500,000, and the phosphate/acrylate copolymer is below its glass transition temperature.

6. The composition of claim 5, wherein the weight average molecular weight is 10,000 to 200,000 grams per mole, optionally, 10,000 to 40,000, 15,000 to 25,000, or 17,000 to 23,000 grams per mole.

7. The composition of claim 1, wherein the whitening agent is a peroxide.

8. The composition of claim 1, wherein the whitening agent is hydrogen peroxide.

9. The composition of claim 1, comprising one or more polyphosphate salts.

10. The composition of claim 1, comprising one or more polyphosphate salts selected from the group consisting of metal hexametaphosphate salts, sodium hexametaphosphate, tripolyphosphate salts, sodium tripolyphosphate, pyrophosphate salts, and sodium acid pyrophosphate.

11. The composition of claim 1, comprising one or more surfactant, one or more detergent, one or more emulsifier, or any combination thereof.

12. The composition of claim 11, wherein the surfactants, detergents and emulsifiers are selected from the group consisting of poloxamers and polysorbates.

13. The composition of claim 11, wherein the surfactants or detergents are poloxamer 407 and polysorbate 20.

14. The composition of claim 1, further comprising one or more antibacterial or antiseptic agents.

15. The composition of claim 14, wherein the antibacterial or antiseptic agents are selected from the group consisting of menthol, methyl salicylate, and combinations thereof.

16. The composition of claim 14, wherein the antibacterial agent is selected from the group consisting of triclosan, cetylpyridinium chloride (CPC), chlorhexidine (CHX), water soluble zinc salts, water insoluble zinc salts, zinc oxide, zinc citrate, stannous salts, and mixtures thereof.

17. The composition of claim 1, wherein the orally acceptable carrier comprises water and humectant selected from one or more of a sugar alcohol, an alkylene glycol, glycerin, or combination thereof.

18. The composition of claim 17, wherein the orally acceptable carrier comprises water, sorbitol and propylene glycol.

19. The composition of claim 1, wherein the composition is a mouth rinse.

20. The composition of claim 1, comprising:
phosphate/acrylate co-polymer in an amount of from 0.1% to 5%;
hydrogen peroxide in an amount of from 0.01% to 4%; and
one or more polyphosphate salts in an aggregate amount of from 0.1% to 3%.

21. The composition of claim 20, wherein, the polyphosphate salts comprise sodium hexametaphosphate.

22. A method for the treatment and/or inhibition of a chemical stain, plaque, acid erosion, and/or tartar on a dental surface, comprising contacting the dental surface with a composition of claim 1.

23. A method for the treatment and/or inhibition of gum disease comprising contacting the oral cavity with a composition of claim 1.

24. A method for the treatment and/or inhibition of halitosis comprising contacting the oral cavity with a composition of claim 1.

25. A method for the inhibition of biofilm formation on a dental surface comprising contacting the oral cavity with a composition of claim 1.

* * * * *